United States Patent [19]
Villalobos

[11] Patent Number: 5,409,464
[45] Date of Patent: Apr. 25, 1995

[54] INTRAVASCULAR CATHETER HAVING BARRIER VALVE

[75] Inventor: Joaquin Villalobos, Miami, Fla.

[73] Assignee: Cordis Corporation, Miami Lakes, Fla.

[21] Appl. No.: 242,186

[22] Filed: May 13, 1994

[51] Int. Cl.⁶ .......................................... A61M 25/00
[52] U.S. Cl. ................................. 604/167; 604/236; 604/256
[58] Field of Search .............. 604/280, 164, 165, 167, 604/168, 169, 256, 236; 137/846, 849

[56] References Cited

U.S. PATENT DOCUMENTS

| | | |
|---|---|---|
| 4,000,739 | 1/1977 | Stevens . |
| 4,421,296 | 12/1983 | Stephens . |
| 4,436,519 | 3/1984 | O'Neill . |
| 4,798,594 | 1/1989 | Hillstead ............... 604/167 |
| 4,895,565 | 1/1990 | Hillstead . |
| 4,960,412 | 10/1990 | Fink ................... 604/256 X |
| 5,176,652 | 1/1993 | Littrell ................. 604/167 |
| 5,304,156 | 4/1994 | Sylvanowicz et al. ...... 604/256 |
| 5,312,362 | 5/1994 | Pfolsgraf et al. ......... 604/167 |

*Primary Examiner*—John D. Yasko
*Attorney, Agent, or Firm*—Gerstman, Ellis & McMillin, Ltd.

[57] ABSTRACT

An intravascular catheter comprises a proximal housing carried on a tubular catheter body. The housing carries a slit, elastomeric partition valve which comprises a barrier wall positioned to block flow through the lumen of the catheter body, while permitting an elongated member such as a catheter to pass through the valve into the lumen without substantial-back leakage of blood. The slit comprises a plurality of intersecting radii which rotate in spiral manner as the slit extends through the barrier wall to define a slit shaped of the intersecting radii of a first diameter on one side of the barrier wall. The slit spirals down to a lesser diameter on the other side of the barrier wall. Thus, advancement of a catheter or the like through the valve is facilitated, and back-leakage through the valve around the catheter is suppressed. Specifically, the intravascular catheter of this invention may be a catheter sheath introducer.

13 Claims, 1 Drawing Sheet

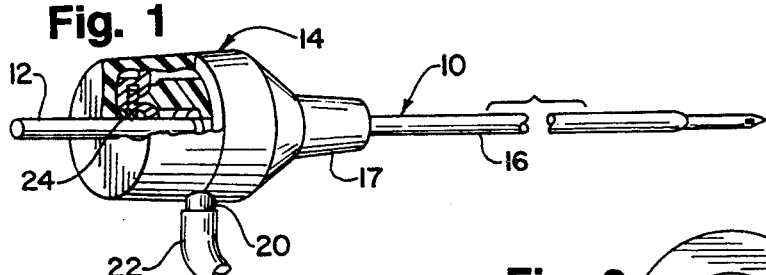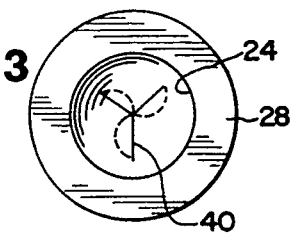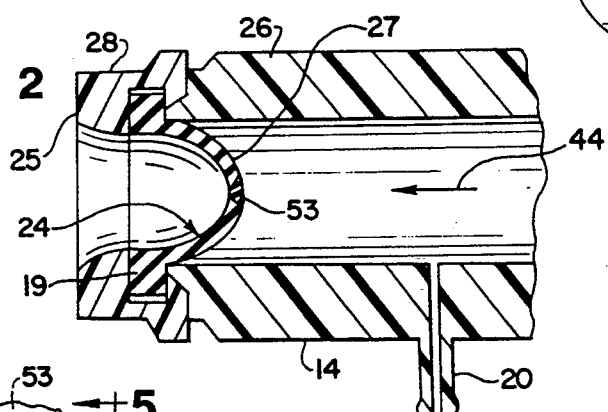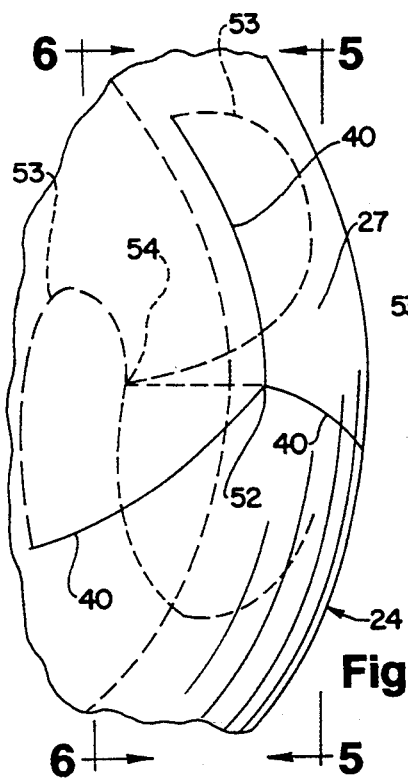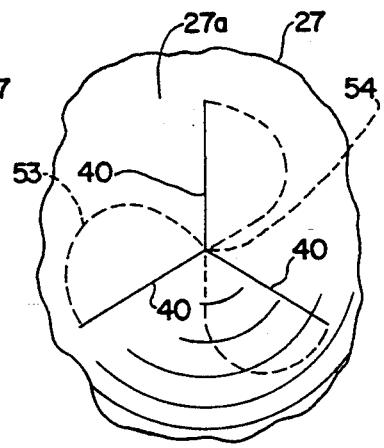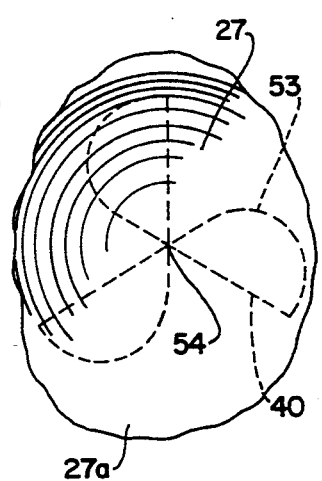

INTRAVASCULAR CATHETER HAVING BARRIER VALVE

BACKGROUND OF THE INVENTION

Intravascular catheters are used to penetrate the vascular system of a patient for a wide variety of therapeutic purposes. Particularly with those catheters which penetrate the arterial side of the cardiovascular system, steps must be taken to prevent back leakage of blood out of and along the catheter because of the higher arterial pressures.

To accomplish this, it has been conventional to provide a catheter sheath introducer such as is disclosed in Stevens U.S. Pat. Nos. 4,000,739 and 4,421,296, Hillstead U.S. Pat. No. 4,895,565, and the like. This type of arterial catheter, the catheter sheath introducer, has a relatively short catheter shaft, a proximal housing, and an elastomeric partition valve secured in the housing and carrying a slit. Thus, another catheter can extend through the slit in the partition valve, and through the entire catheter sheath introducer, to be inserted into the arterial system of the patient while the elastomeric partition valve prevents the back bleeding of blood through the annular space that exists between the two catheters.

Catheters may be inserted and withdrawn through the catheter sheath introducer, which reduces trauma to the patient relating to the repeated motion of catheters in the arterial system. Additionally, guidewires may be inserted through the catheter sheath introducer into the arterial system of the patient.

Disadvantages have been noted in previous designs of catheter sheath introducers, in that some slit configurations do not stop the leakage well. Also, it is desirable for the friction to be minimized as a catheter advances through the elastomeric partition valve. If the friction is high, the manipulation of catheters through it is impeded, and the partition valve may rip, causing it to fail.

By this invention, a new design of elastomeric partition valve for a catheter sheath introducer, or any other desired intravascular catheter, is provided. The new elastomeric partition valve exhibits a very low advancing friction when a catheter or a guidewire is being advanced through and into the patient. However, the same partition valve exhibits an improved capability to resist back leakage of blood at arterial pressures, when compared with other types of partition valves for this purpose.

DESCRIPTION OF THE INVENTION

In accordance with this invention, an intravascular catheter is provided which comprises a proximal housing carried on a tubular catheter body. The housing carries an elastomeric partition valve which comprises a slit barrier wall. The barrier wall is positioned to block flow through the lumen of the catheter body while permitting an elongated member to pass through the valve into the lumen without substantial back-leakage of blood.

The partition valve typically defines a peripheral edge portion that is secured with the housing. Particularly, it may be held with an annular, pressurized seal between two components of the housing.

The slit of the barrier wall may comprise a plurality of intersecting radii which rotate in spiral manner as the slit extends through the barrier wall, to define a slit shaped of the intersecting radii on one side of the barrier wall, but the slit spirals down to a lesser dimension or a substantial point on the other side of the barrier wall. It is preferred for the one side of the barrier wall to be the distal side, so that the slit of substantial point or lesser dimension is on the proximal side. This magnifies the unidirectional tendency of the valve to present high resistance to fluids trying to escape through the valve in the proximal direction.

The partition valve can define a barrier wall having a central, slit portion which projects distally toward the catheter body from a peripheral edge portion of the barrier wall. With this modification, the advancement of an elongated member through the valve is further facilitated with reduced friction. At the same time, back leakage through the valve around the elongated member can be effectively suppressed.

The slit barrier wall may preferably define a distally projecting central section which is substantially spherical in shape. The slit is defined in this central section.

DESCRIPTION OF DRAWINGS

In the drawings, FIG. 1 is a perspective view of a catheter sheath introducer in accordance with this invention;

FIG. 2 is an enlarged, fragmentary, longitudinal sectional view of the proximal end of the catheter sheath introducer of FIG. 1;

FIG. 3 is an enlarged, elevational view of the proximal end of the catheter sheath introducer of FIG. 1;

FIG. 4 is an enlarged perspective view of the distal tip of the partition valve of this invention;

FIG. 5 is a view taken along line 5—5 of FIG. 4; and

FIG. 6 is a view taken along line 6—6 of FIG. 5.

DESCRIPTION OF SPECIFIC EMBODIMENTS

Referring to the FIGS. 1—3, FIG. 1 shows a catheter sheath introducer 10 adapted to receive an inner catheter 12 as shown for insertion into the vascular system of a patient. Catheter sheath introducer 10 is used to introduce a catheter 12 into a blood vessel, while preventing blood backflow along the outside surface of catheter 12.

Catheter sheath introducer 10 defines outer tubular housing 14, which carries catheter body portion 16 of catheter sheath introducer 10, positioned in attached, telescoping relation with tubular protrusion 17 of the housing. Side port 20 may be of conventional design, being adapted for telescoping connection with plastic tubing 22, for providing saline solution for flushing the interior of housing 14 and catheter body 16, or for withdrawing a blood sample.

Housing 14 also carries a self sealing, penetrable barrier member 24, which may be made of an appropriate elastomeric material such as silicone rubber, especially one of high elongation and tensile strength, i.e., an elongation to break of about 900 to 1500 percent as measured by ASTM D412; a tensile strength of about 11.5 to 15 megapascals as measured by ASTM D412; and a Shore A durometer of about 45 to 70 as measured by ASTM D2240. For example Dow Corning Silastic Q7-47-50 or 65 medical grade ETR elastomer may be used, having a Die B tear strength of at least about 150 pounds per inch as determined by ASTM D624, as described in Goode et al. U.S. patent application Ser. No. 08/077,242, filed Jun. 14, 1993 and entitled Enhanced Sheath Valve.

Housing 14 may comprise casing portions 26, 28, which are sealed together in telescoping relation and which peripherally capture a peripheral edge portion 19 of barrier member 24 between them in a pressure seal as shown. Alternatively, casing portion 28 may be a screw cap, for adjustable, compressive retention of barrier 24. Annular ribs may be provided in each housing portion to provide more positive capture of the periphery of elastomeric barrier 24.

A central portion 27 of barrier wall portion 24 projects distally toward catheter body 16 to preferably define a distally projecting, substantially spherical end section.

Slits 40 may comprise a plurality of preferably three to six intersecting radii which rotate in spiral manner as the slit extends through the barrier wall 24.

As shown in FIGS. 4-6, central portion 27 of barrier wall member 24 may define a distal side which, in turn, defines slits 40 which comprise a plurality of intersecting radii meeting at a central origin 52. Slits 40 extend through barrier wall member 24, but in a spiral manner rather than the helical manner of the prior art, tapering down to an effective spiral point 54 at the other, proximal side of barrier wall member 24. The outer end of each spiral, slit line 40 is represented by reference numeral 53 in FIGS. 4-6.

A pair of intersecting, radial slits 40 may comprise a single line or diameter, if desired, at an angle of 180°.

As FIG. 5 shows, the distal, convex, central portion 27 of the barrier wall shows three radial slits. FIG. 6 shows the concave, proximal face of central portion 27, which is smooth and unslit, except for the substantial point 54 which comprises the spiral end of the inwardly spiralling slits 40. If desired, substantial point 54 may be perceptibly larger than a point. The term is intended to indicate configurations which are of much less radius than the radial slits 40 on the opposed side of barrier wall portion 24.

Because of the concave configuration of barrier wall 24 from the perspective of the proximal housing end 25, an elongated member such as catheter 12 or a guidewire will engage the concave side of barrier wall 24, which imparts expansive forces to the barrier wall, tending to more easily spread the various parts defining slit or slits 40, for easy and low friction penetration thereof by catheter 12 or the like.

However, when blood under arterial pressure moves outwardly along the direction indicated at 44 in FIG. 2, such blood or other pressurized fluid encounters a convex surface. Thus, in this circumstance the pressure forces the various portions that define slit or slits 40 together, tending to increase the sealing characteristics of the valve over a similar elastomeric partition which is planar. Thus, reduced catheter advancing friction is achieved, coupled with improved fluid sealing in accordance with this invention.

Barrier wall 24 may be of a diameter and thickness which is conventional for barrier walls used in catheter sheath introducers. Also, barrier wall 24 may be flat if desired, rather than forming a dome as shown.

The above has been offered for illustrative purposes only and is not intended to limit the scope of the invention, which is as defined in the claims below.

That which is claimed is:

1. An intravascular catheter which comprises a proximal housing carried on a tubular catheter body, said housing carrying a slit, elastomeric partition valve comprising a barrier wall positioned to block flow through the lumen of said catheter body while permitting an elongated member to pass through said valve into said lumen without substantial back-leakage of blood, said slit comprising a plurality of intersecting radii which rotate in spiral manner as said slit extends through said barrier wall, to define a slit shaped of said intersecting radii on one side of said barrier wall, said slit spiralling down to a substantial point on the other side of said barrier wall, whereby advancement of an elongated member through said valve is facilitated, and back-leakage through said valve around said elongated member is suppressed.

2. The catheter of claim 1 in which said one side of the barrier wall is the distal side.

3. The catheter of claim 1 in which a central portion of said barrier wall projects distally toward said catheter body from a peripheral edge portion of said barrier wall.

4. The catheter of claim 3 in which said distally projecting, central, slit barrier wall portion defines a distally projecting, substantially spherical end section, said slit being defined in said end section.

5. The catheter of claim 1 in which said barrier wall is made of silicone rubber.

6. An intravascular catheter which comprises a proximal housing carried on a tubular catheter body, said housing carrying a slit, elastomeric partition valve comprising a barrier wall positioned to block flow through the lumen of said catheter body while permitting an elongated member to pass through said valve into said lumen without substantial back-leakage of blood, said slit comprising a plurality of intersecting radii which rotate in spiral manner as said slit extends through said barrier wall, to define a slit shaped of said intersecting radii on the distal side of said barrier wall, said slit spiralling down to a substantial point on the proximal side of said barrier wall, a central portion of said barrier wall projecting distally toward said catheter body from a peripheral edge portion of said barrier wall, whereby advancement of an elongated member through said valve is facilitated, and back leakage through said valve around said elongated member is suppressed.

7. The catheter of claim 6 in which said distally projecting, central, slit barrier wall portion defines a distally projecting, substantially spherical end section, said slit being defined in said end section.

8. The catheter of claim 6 in which the barrier wall is made of silicone rubber.

9. An intravascular catheter which comprises a proximal housing carried on a tubular catheter body, said housing carrying a slit, elastomeric partition valve comprising a barrier wall positioned to block flow through the lumen of said catheter body while permitting an elongated member to pass through said valve into said lumen without substantial back leakage of blood, said slit comprising a plurality of intersecting radii which rotate in spiral manner as said slit extends through said barrier wall to define a slit shaped of said intersecting radii of a first length on one side of said barrier wall, said slit spiralling down to radii of a lesser length on the other side of said barrier wall, whereby advancement of an elongated member through said valve is facilitated, and back-leakage through said valve around said elongated member is suppressed.

10. The catheter of claim 9 in which said one side of the barrier wall is the distal side.

11. The catheter of claim 9 in which a central portion of said barrier wall projects distally toward said catheter body from a peripheral edge portion of said barrier wall.

12. The catheter of claim 11 in which said distally projecting, central, slit barrier wall portion defines a distally projecting, substantially spherical end section, said slit being defined in said end section.

13. The catheter of claim 9 in which said barrier wall is made of silicone rubber.

* * * * *